United States Patent [19]

Fischer et al.

[11] Patent Number: 5,597,407

[45] Date of Patent: *Jan. 28, 1997

[54] METHOD OF THICKENING AQUEOUS FORMULATIONS

[75] Inventors: Stephen A. Fischer, Yardley; Kartar S. Arora, Chalfont; Reuben Grinstein, Blue Bell; Patrick M. McCurry, Jr., Lansdale; Judith C. Giordan, Villanova, all of Pa.

[73] Assignee: Henkel Corporation, Plymouth Meeting, Pa.

[ * ] Notice: The term of this patent shall not extend beyond the expiration date of Pat. No. 5,597,406.

[21] Appl. No.: 458,307

[22] Filed: Jun. 2, 1995

Related U.S. Application Data

[62] Division of Ser. No. 146,549, Nov. 2, 1993, Pat. No. 5,501,813.

[51] Int. Cl.$^6$ .............. G05D 24/00; C11D 1/72; C11D 3/20; C11D 1/74

[52] U.S. Cl. .............. 106/237; 106/238; 106/215.1; 510/158; 510/159; 510/119; 510/127; 510/422; 510/424; 510/426; 510/427; 510/432; 510/436

[58] Field of Search ............. 252/174.17, DIG. 1, 252/DIG. 14, 550, 162, 172, 173, 174.18, 174.21, 174.22, DIG. 17, 135, 174.23, 174.24, DIG. 13, DIG. 2, 170; 514/777, 845; 106/206, 208, 25 R, 237, 238

[56] References Cited

U.S. PATENT DOCUMENTS

| | | | |
|---|---|---|---|
| 3,435,024 | 3/1969 | Nobile et al. | 260/210 |
| 3,562,300 | 2/1971 | Chao et al. | 260/398 |
| 3,956,198 | 5/1976 | Bauer | 252/DIG. 14 |
| 4,098,713 | 7/1978 | Jones | 252/DIG. 1 |
| 4,239,641 | 12/1980 | Perner et al. | 252/142 |
| 4,483,779 | 11/1984 | Llenado et al. | 252/174.17 X |
| 4,536,318 | 8/1985 | Cook et al. | 252/174.17 |
| 4,663,069 | 5/1987 | Llenado | 252/174.17 X |
| 4,732,696 | 3/1988 | Urfer | 252/174.17 |
| 4,803,010 | 2/1989 | Ogino et al. | 252/174.21 |
| 5,015,471 | 5/1991 | Birtwistle et al. | 252/DIG. 14 |
| 5,192,462 | 3/1993 | Gloor et al. | 252/174.21 |
| 5,230,835 | 7/1993 | Deguchi et al. | 252/174.21 X |
| 5,266,690 | 11/1993 | McCurry et al. | 252/174.17 X |
| 5,275,761 | 1/1994 | Bergmann | 252/174.21 X |
| 5,358,667 | 10/1994 | Bergmann | 252/174.17 X |
| 5,403,517 | 4/1995 | Horinishi et al. | 252/174.21 X |
| 5,478,490 | 12/1995 | Russo et al. | 252/174.17 X |
| 5,501,813 | 3/1996 | Fischer et al. | 252/174.17 |

FOREIGN PATENT DOCUMENTS

| | | |
|---|---|---|
| 511466 | 11/1992 | European Pat. Off. . |
| 4026809 | 2/1992 | Germany . |
| 4036663 | 5/1992 | Germany . |
| 4137317 | 5/1993 | Germany . |
| 4227203 | 10/1993 | Germany . |

OTHER PUBLICATIONS

Emulsifiers & Detergents, McCutcheon's Division, International, p. 188.

*Primary Examiner*—Douglas J. McGinty
*Attorney, Agent, or Firm*—Wayne C. Jaeschke; John E. Drach; Steven J. Trzaska

[57] ABSTRACT

A composition for thickening aqueous based personal care products is comprised of a cosolvent selected from the group consisting of a diol, the mono alkyl ether of a diol, a salt of a sulfated ethoxylated alcohol, a salt of a sulfated ethoxylated alkyl phenol, and a complex organic phosphate ester; water; a nonionic surfactant and, an ester of an ethoxylated polyol.

17 Claims, No Drawings

METHOD OF THICKENING AQUEOUS FORMULATIONS

This application is a divisional of U.S. appl. Ser. No. 08/146,549, filed Nov. 2, 1993, now U.S. Pat. No. 5,501,813.

BACKGROUND OF THE INVENTION

1. Field of the Invention

This invention relates to thickeners for increasing the viscosity of aqueous compositions. In particular, this invention relates to thickeners which are easily incorporated into aqueous-based cosmetics and latex paints.

2. Description of the Related Art

Many aqueous systems require thickeners in order to be useful for various types of applications. Such aqueous-based systems as cosmetics, protective coatings for paper and metal, printing inks, and latex paints all require the incorporation of thickeners in order to have the proper rheological characteristics for their particular uses. Many substances useful as thickeners are known in the art. These include natural polymers such as casein and alginates, and synthetic materials such as cellulose derivatives, acrylic polymers, and polyurethane polymers. Some thickeners for use in personal care products such as shampoos, facial cleaners, liquid hand soaps, and the like require prolonged mixing periods and high temperatures to be incorporated into the products to be thickened. In some instances, the effectiveness of some thickeners has been found to be influenced by the components in the compositions to be thickened. Thus, there is a need for thickeners for aqueous-based personal care products which are readily incorporated and whose efficacy is not affected by other components such as salts.

SUMMARY OF THE INVENTION

Highly efficient thickeners have been surprisingly discovered that are easily incorporated into aqueous-based personal care formulations at temperatures as low as 20° C. and without the need for heating and prolonged mixing. These thickeners contain: (a) a cosolvent selected from the group consisting of a diol, the mono alkyl ether of a diol, a salt of a sulfated ethoxylated alcohol, a salt of a sulfated ethoxylated alkyl phenol, and a complex organic phosphate ester; (b) water; (c) a nonionic surfactant having an HLB of less than about 14; (d) an ester of an ethoxylated polyol having at least 3 alcohol groups and having degree of ethoxylation from about 80 to about 400. The thickeners according to the invention are very versatile in that they can be used to thicken such personal care products as shampoos, liquid hand soaps, showers gels, facial cleansers, and bubble bath soaps while also functioning as temporary thickeners for acrylic latex paints.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The cosolvents which can be used according to the invention are selected from the group consisting of a diol, the mono alkyl ether of a diol, a salt of a sulfated ethoxylated alcohol, a salt of a sulfated ethoxylated alkyl phenol, and a complex organic phosphate esters which are a mixture of mono- and di-esters of phosphoric acid wherein the ester groups are ethoxylated alcohols or ethoxylated alkyl phenols or a combination thereof.

A diol can be any saturated or unsaturated, linear, branched, or cyclic compound having 2 alcohol functionalities. Examples of such diols include, but are not limited to, ethylene glycol, 1,2-propanediol, 1,3-propanediol, 1,2-butanediol, 1,3-butanediol, 1,4-butanediol, 1,5-pentanediol, 1,6-hexanediol, 1,10-decanediol, 1,12-dodecanediol, 2-methyl-1,2-propanediol, 1,2-cyclopentanediol, 1,3-cyclopentanediol, 1,2-cyclohexanediol, 1,3-cyclohexanediol, 1,4-cyclohexanediol, diethylene glycol, triethyleneglycol, PEG-200 (polyethyleneglycol-200), and PEG-400 (polyethyleneglycol-400).

The alkyl group of the mono alkyl ether of a diol has from 1 to 10 carbon atoms and can be any mono ether derivative of any of the diols set forth above or a mono ether of a polyethylene glycol having a molecular weight of less than 700. Examples of such compounds include but are not limited to 2-methoxyethanol (the mono methyl ether of ethylene glycol), 2-butoxyethanol (the mono butyl ether of ethylene glycol), butyl carbitol (monobutyl ether of diethylene glycol), butoxytriglycol (monobutyl ether of triethylene glycol), methoxy PEG-200 (mono methyl ether of polyethyleneglycol-200), methoxy PEG-350 (mono methyl ether of polyethyleneglycol-350). In thickener compositions for personal care products, the preferred cosolvents are 1,2-propanediol, PEG-200, PEG-400, and methoxy PEG-350.

A salt of a sulfated ethoxylated alcohol can be the alkali metal sulfate salt or ammonium sulfate salt of an ethoxylated alcohol wherein the alcohol is a saturated or unsaturated aliphatic alcohol having from 6 to 22 carbon atoms or a phenol or an alkyl phenol. Such compounds are available commercially, for example from Rhone-Poulenc Surfactant and Specialty Division, Cranberry, N.J., as Alipal® CO433 which is the sodium salt of a sulfated polyethoxynonylphenol, Alipal® CO436 which is the ammonium salt of a sulfated polyethoxynonylphenol, Alipal® EO526 sodium salt of a sulfated alkylphenoxypolyethyleneoxy ethanol.

Complex organic phosphate esters which are a mixture of mono- and di-esters of phosphoric acid wherein the ester groups are ethoxylated alcohols or ethoxylated alkyl phenols are available commercially, for example from Rhone-Poulenc Surfactant and Specialty Division, Cranberry, N.J., as Gafac® RA600, Gafac® BH650, and Gafac® BI729, each of which is a free acid of a complex organic phosphate ester. The compositions according to the invention can contain up to 25% by weight of any one or a combination of cosolvents.

The nonionic surfactant component according to the invention can be any nonionic surfactant or combinations thereof having an HLB value of less than 14 as determined experimentally or calculated by the following Equations I or II $$HLB = E/5 \qquad (I)$$

Equation I is used to calculate the HLB value of a surfactant where only ethylene oxide is used to produce the hydrophilic moiety. In Equation I, E is the weight percent of the oxyethylene content. Equation II $$HLB = 20(1 - S/A) \qquad (II)$$

is used to calculate the HLB of fatty acid esters of polyhydric alcohols wherein S is the saponification number of the ester and A is the acid number of the acid.

One class of particularly preferred nonionic surfactants are alkyl polyglycosides. The alkyl polyglycosides which can be used in the compositions according to the invention have the formula I

$$R_1O(Z)_a \qquad\qquad I$$

wherein $R_1$ is a monovalent organic radical having from about 6 to about 30 carbon atoms; Z is saccharide residue having 5 or 6 carbon atoms; a is a number having a value from 1 to about 6. The alkyl polyglucosides which can be used in the compositions according to the invention have the formula I and are commercially available, for example, as APG®, Glucopon®, or Plantaren® surfactants from Henkel Corporation, Ambler, Pa., 19002. Examples of such surfactants include but are not limited to:

1. APG® 225 Surfactant—an alkylpolyglycoside in which the alkyl group contains 8 to 10 carbon atoms and having an average degree of polymerization of 1.7.

2. APG® 425 Surfactant—an alkyl polyglycoside in which the alkyl group contains 8 to 16 carbon atoms and having an average degree of polymerization of 1.6.

3. APG® 625 Surfactant—an alkyl polyglycoside in which the alkyl groups contains 12 to 16 carbon atoms and having an average degree of polymerization of 1.6.

4. APG® 300 Surfactant—an alkyl polyglycoside substantially the same as APG® 325 Surfactant but having an having an average degree of polymerization of 1.4.

5. APG® 325 Surfactant—an alkyl polyglycoside in which the alkyl groups contains 9 to 11 carbon atoms and having an average degree of polymerization of 1.6.

6. Glucopon® 600 Surfactant—an alkyl polyglycoside in which the alkyl groups contains 12 to 16 carbon atoms and having an average degree of polymerization of 1.4.

7. Plantaren® 2000 Surfactant—a $C_{8-16}$ alkyl polyglycoside in which the alkyl group contains 8 to 16 carbon atoms and having an average degree of polymerization of 1.4.

8. Plantaren® 1300 Surfactant—a $C_{12-16}$ alkyl polyglycoside in which the alkyl groups contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is zero; b is a number from 1.8 to 3; and $R^1$ is an alkyl radical having from 8 to 20 carbon atoms. The composition is characterized in that it has increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglucosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in copending application Ser. No. 07/810,588, filed on Dec. 19, 1991, the entire contents of which are incorporated herein by reference.

Examples of combinations of nonionic surfactants include a mixture of an alkyl polyglycoside and an ethoxylated alkyl phenol, a mixture of an alkyl polyglycoside and an ethoxylated fatty alcohol, and the like. Combinations comprised of an alkyl polyglycoside of the formula I and nonylphenol EO-9 (nonylphenol ethoxylated with 9 moles of EO on average); an alkyl polyglycoside of the formula I and decyl alcohol EO-6 (decyl alcohol ethoxylated with 6 moles of EO on average); are preferred. The compositions according to the invention can contain up to 60% by weight of any one or a combination of nonionic surfactants.

The thickener according to the invention contains a carboxylic acid ester of an ethoxylated polyol. For purposes of the present invention, a carboxylic acid ester of an ethoxylated polyol can be a single carboxylic acid ester of an ethoxylated polyol or a mixture of a large number of such esters wherein each component of the mixture is a carboxylic acid ester of an ethoxylated polyol having a definite degree of ethoxylation and/or a definite degree of esterification. For example, a sample of an isostearic acid ester of ethylene glycol having an average degree of ethoxylation of 100 may contain a single compound wherein each molecule is a di-isostearic acid ester of ethylene glycol wherein each alcohol group is ethoxylated with 100 oxyethylene units. The sample may also contain a mixture of compounds comprised of at least the mono-isostearic acid ester of ethylene glycol having an average degree of ethoxylation of 100 and di-isostearic acid ester of ethylene glycol having an average degree of ethoxylation of 100. The degree of ethoxylation is stated as an average because, in the ethoxylation reaction, a distribution of polyethoxylation is invariably obtained. Such esters can be made, for example, by esterifying an ethoxylated polyol having an average degree of ethoxylation of from 80 to 400 with a fatty acid having from 6 to 22 carbon atoms. The esterification reaction can be carried out by any means known to those skilled in the art such as by direct esterification with a fatty acid or by transesterification of a fatty acid ester or by reaction with a fatty acid halide. An ethoxylated polyol is any compound having at least 3 alcohol groups wherein the majority of the alcohol functionalities have been etherified with polyoxyethylene. Examples of the polyols which can be used to make the ethoxylated polyols according to the invention include, but are not limited to, trimethylolethane [2-methyl-2-(hydroxymethyl)-1,3-propanediol], trimethylolpropane [2-ethyl-2-(hydroxymethyl)-1,3-propanediol], and pentaerythritol (2,2-dimethylol-1,3-propanediol), diglycerol (glycerol dimer), dipentaerythritol, glycerol, and the like. An alkyl polyglycoside as set forth above can also serve as a polyol which can be ethoxylated and used in the compositions according to the invention. Ethoxylated polyols can be made by any method known to those skilled in the art such as by the direct ethoxylation of a polyol as disclosed in Example 1. The preferred esters of ethoxylated polyols are pentaerythritol PEG-120 tetra C12–C18 ester which is an ethoxylated pentaerythritol having an average degree of ethoxylation of 120 esterified with an average of 4 moles of fatty acid mixture comprised of fatty acids having from 12 to 18 carbon atoms; pentaerythritol PEG-90 tetra isostearate which is an ethoxylated pentaerythritol having an average degree of ethoxylation of 90 esterified with an average of 4 moles of isostearic acid; and pentaerythritol PEG-130 tetra isostearate which is an ethoxylated pentaerythritol having an average degree of ethoxylation of 130 esterified with an average of 4 moles of isostearic acid; and pentaerythritol PEG-120 tetra isostearate. The compositions according to the invention can contain up to 50% by weight of any one or a combination of an ester of an ethoxylated polyol.

The amount of thickener according to the invention which can be used to thicken aqueous compositions such as personal care products which includes shampoos, facial cleaners, liquid hand soaps, and the like will vary according to the composition of the product to be thickened and is readily determinable by one of ordinary skill in the art. A thickening effective amount will typically range from 0.1% to 5.0% by weight.

The thickener compositions according to the invention can be made by mixing the cosolvent, water, nonionic surfactant and, esterified ethoxylated polyol using standard mixing equipment.

The following examples are meant to illustrate but not to limit the invention.

EXAMPLE 1

Preparation of Pentaerythritol PEG-120 Tetraisostearate

In a 3 liter reaction flask equipped with an agitator, distillation condenser, nitrogen and temperature inlets, 2,698 grams (30.6 moles) of ethylene carbonate was heated to 65°–70° C. Pentaerythritol (1,302 grams, 9.57 moles) was added and the reaction mass was heated to 100°–110° C. After adding 8 grams of potassium hydroxide, starting a nitrogen sweep, and raising the temperature to 150°–160° C., the contents were reacted for 2 hours. The temperature was raised to 185°–190° C. and the reaction continued until a hydroxyl number of 810.7 mg KOH/g was reached. A vacuum strip at 185° C. was used to remove any volatiles before the product was discharged. A portion of the reaction material (260 grams, 0.939 mole, hydroxyl number=810.7 mg KOH/g) was transferred to an ethoxylation vessel and 3.6 grams of potassium hydroxide was added. Its contents were degassed and dried at 115°–120° C. to a moisture of 0.08%. Ethylene oxide was introduced at 140°–150° C. and reacted to a hydroxyl number of 43 mg KOH/g, at which time, the reaction was stopped and 3.8 grams of acetic acid was added. The product had a final hydroxyl value of 43 mg KOH/g and an acid value of 1.63 mg KOH/g. In a 0.25 liter reaction flask equipped with an agitator, reflux condenser, nitrogen and temperature inlets, 100 grams (0.077 equivalents OH) ethoxylated pentaerythritol (hydroxyl number=43 mg KOH/g), 0.2 gram Fascat-4100, 0.3 gram 37% hydrochloric acid, and 24.1 grams (0.076 mole) of isostearic acid having an acid value of 178.05 mg KOH/g were added were heated to 200° C. The reaction was stopped when the acid value was less than 1.25 mg KOH/g.

EXAMPLE 2

Preparation of Pentaerythritol PEG-120 Tetralaurate

The procedure of Example 1 was repeated except that 0.076 mole of lauric acid was substituted for the isostearic acid.

EXAMPLE 3

Preparation of Pentaerythritol PEG-120 Esterified with A $C_{12}$–$C_{18}$ Fatty Acid Mixture The procedure of Example 1 was repeated except that 0.076 mole of a $C_{12}$–$C_{18}$ fatty acid mixture was substituted for the isostearic acid.

EXAMPLE 4

Preparation of $C_{10}$–$C_{18}$ Alkyl Polyglycoside PEG-120 Esterified with Isostearic Acid The procedure of Example 1 was repeated except that a C10-C18 alkyl polyglycoside was substituted for pentaerythritol.

EXAMPLE 5

Preparation of Pentaerythritol PEG-90 Tetraisostearate

The procedure of Example 1 was repeated with a pentaerythritol ethoxylate having a hydroxyl number of 52 mg KOH/g. The ethoxylate was reacted with isostearic acid at a 1:1 equivalent ratio. The final ester had an acid value of 0.86 mg KOH/g.

EXAMPLE 6

Preparation of Pentaerythritol PEG-130 Tetraisostearate

The procedure of Example 1 was repeated with a pentaerythritol ethoxylate having a hydroxyl number of 39 mg KOH/g. The ethoxylate was reacted with isostearic acid at a 1:1 equivalent ratio. The final ester had an acid value of 1.25 mg KOH/g.

EXAMPLE 7

Preparation of Thickener Concentrate

The products in Examples 1 and 3–6 were blended with different nonionic surfactants, water, and cosolvents. The thickener compositions and their dispersability in surfactant solutions are listed in Table 1. Tables 2 and 3 lists thickening data of thickener compositions in shampoo formulations.

EXAMPLE 8

Thickening a Latex Paint

A thickener concentrate (1.6 grams) having a composition of 40% decyl-6EO alcohol, 35% pentaerythritol PEG-120 tetraisostearate, 15% propylene glycol, and 10% water (Table 1, thickener j) thickened 60.0 grams of a styrene-acrylic latex paint from 90 cps (containing no thickener) to 4,350 cps.

EXAMPLE 9

Thickening of an Alkyl Polyglycoside Surfactant

A thickener concentrate (1.6 grams) having a composition of 40% $C_{12}$–$C_{16}$ 2EO alcohol, 35% pentaerythritol PEG-120 tetraisostearate, 15% propylene glycol, and 10% water (Table 1, thickener m) thickened 60.0 grams of Plantaren® 2000 Surfactant from 976 cps (containing no thickener) to 1,480 cps.

EXAMPLE 10

Thickening of Shampoo Formulations

Shampoo Formulation A

40% by weight of 26% sodium lauryl ether sulfate solution; 3% by weight of cocamide diethanol amine; and 57% by weight of water. The pH was adjusted to 6.5 with citric acid.

Shampoo Formulation B 15.0% Plantaren® 2000 (50% decyl polyglucose solution)

15.0% Standapol® EA-2 (26% ammonium laureth sulfate)

12.5% Velvetex® BK-35 (cocamidopropyl betaine)

1.5% Nutrilan® I (hydrolyzed collagen)

56.0% water. The pH was adjusted to 6.5 with citric acid.

TABLE 1

Thickener compositions

| Comp. | % ppeg-tis | % co-solvent | % water | type of nonionic surfactant | % nonionic surfactant | shampoo formula | soluble[4] |
|---|---|---|---|---|---|---|---|
| a | 40[1] | — | 10 | NP9 | 50 | A | NO |
| b | 35[1] | — | 10 | NP9 | 55 | A | NO |
| c | 30[1] | — | 10 | NP9 | 60 | A | NO |
| d | 30[1] | 13[13] | 10 | NP9 | 47 | A, B | YES |
| e | 54 | 36[15] | 10 | — | — | A, B | NO |
| f | 35 | 28[13] | 7 | NP9 | 30 | A, B | YES |
| g | 25 | 20[15] | 15 | APG-225 DA6 | 17.5 22.5 | A, B | YES |
| h | 25 | 20[15] | 20 | APG-425 DA6 | 12.5 22.5 | A, B | YES |
| i | 26 | 11[15] | 14 | APG-625 NP9 | 14.0 35.0 | A, B | YES |
| j | 35 | 15[15] | 10 | DA6 | 40 | A, B | YES |
| k | 35 | 15[15] | 10 | $C_{(12-14)}$-2 | 40 | A, B | YES |
| l | 35 | 15[15] | 10 | S-7[5] | 40 | A, B | YES |
| m | 35 | 15[15] | 10 | $C_{(12-14)}$-2 | 40 | B | YES |
| n | 35 | 15[15] | 10 | $C_{(9-11)}$-6 | 40 | A, B | YES |
| o | 35[2] | 15[15] | 10 | DA6 | 40 | A, B | YES |
| p | 35 | 15[5] | 10 | DA6 | 40 | A, B | YES |
| q | 35 | 15[6] | 10 | DA6 | 40 | B | YES |
| r | 35 | 15[7] | 10 | DA6 | 40 | A, B | YES |
| s | 35 | 15[8] | 10 | DA6 | 40 | B | YES |
| t | 35 | 15[9] | 10 | DA6 | 40 | B | YES |
| u | 35 | 15 | 10 | NP12 | 40 | B | NO |
| v | 35 | 15 | 10 | T-80[12] | 40 | B | NO |
| w | 35 | — | 16 | DA6 | 49 | A, B | NO, YES |
| x | 35 | 15 | 10 | S-9[11] | 40 | B | YES |
| y | 35[13] | 15 | 10 | DA6 | 40 | A, B | YES |
| z | 35[14] | 15 | 10 | DA6 | 40 | A, B | YES |
| aa | 35[10] | 15 | 10 | DA6 | 40 | A, B | YES |
| bb | 35[14] | 15[16] | 10 | DA6 | 40 | A, B | YES |
| cc | 50 | 37[17] | 15 | — | — | A | NO |

Key to Table 1
PPEG-TIS = pentaerythritol PEG-120 tetra isostearate
PG = propylene glycol
NP9 = nonylphenol ethoxylate, 9 EO (HLB = 13)
NP12 = nonylphenol ethoxylate, 12 EO (HLB = 14.2)
DA6 = decyl alcohol ethoxylate, 6 EO (HLB 12.5)
APG = alkyl polyglycoside (HLB = 12–13)
$C_{(12-14)}$-X = mixed linear ethoxylated alcohols, X moles EO
[1]pentaerythritol PEG-120 tetra C12–C18 ester
[2]alkyl polyglucose ethoxylate isostearate
[3]C10–C15 secondary alcohol ethoxylate, 7 moles EO
[4]instant solubility in shampoo formula at 25° C.
[5]butyl carbitol
[6]PEG-200
[7]methoxy PEG-350
[8]ethylene glycol
[9]butoxytriglycol
[10]glucomate DOE-120 (PEG-120 methyl glucoside dioleate)
[11]C10–C15 secondary alcohol ethoxylate, 9 EO (HLB = 13.5)
[12]sorbitan monooleate PEG-20 (HLB = 15)
[13]pentaerythritol PEG-90 tetra isostearate
[14]pentaerythritol PEG-130 tetra isostearate
[15]1,2-propanediol
[16]complex organic phosphate ester
[17]2.5% sodium lauryl ether sulfate, 2-EO + 32.5% 1,2-propanediol

TABLE 2

Thickening Shampoo Formula A[1]

| Blends, Table 1 | % Active | Viscosity, cps |
| --- | --- | --- |
| Blank | — | 25 |
| f | 65 | 3,300 |
| g | 65 | 4,530 |
| h | 60 | 5,000 |
| i | 75 | 5,120 |
| j | 75 | 5,280 |
| l | 75 | 5,800 |
| o | 75 | 1,650 |
| y | 75 | 3,400 |
| z | 75 | 10,300 |
| Commercial Thickener | 100 | 4,560 |

[1] 0.5% NaCl and 1.0% thickener

TABLE 3

Thickening Shampoo Formula B[1]

| Thickener from Table 1 | % Active | Viscosity, cps |
| --- | --- | --- |
| Blank | — | 208 |
| f | 65 | 4,240 |
| g | 65 | 3,350 |
| h | 60 | 2,700 |
| i | 75 | 2,800 |
| j | 75 | 3,100 |
| k | 75 | 5,850 |
| l | 75 | 3,100 |
| m | 75 | 9,400 |
| n | 75 | 4,200 |
| o | 75 | 2,300 |
| p | 75 | 2,600 |
| q | 75 | 3,400 |
| r | 75 | 3,600 |
| s | 75 | 4,950 |
| t | 75 | 3,480 |
| w | 84 | 3,660 |
| x | 75 | 4,050 |
| y | 75 | 2,900 |
| z | 75 | 5,500 |
| aa | 75 | 1,450 |
| Commercial Thickener | 100 | 2,920 |

[1] 0.5% thickener

The following comparative examples show the thickening effect of the same esterified ethoxylated polyol by itself and when incorporated into a composition according to the invention. A thickener according to the invention which contained pentaerythritol PEG-130 tetra isostearate dissolved readily at room temperature in a typical shampoo formulation. Pentaerythritol PEG-130 tetra isostearate alone did not dissolve in a typical shampoo formulation and dissolved only at elevated temperatures and with difficulty.

COMPARATIVE EXAMPLE 1

About 3.4 grams of a thickener z from Table 1 (containing 35% pentaerythritol PEG-130 tetra isostearate) were added to 60 grams of shampoo formulation A. The thickener dissolved instantly in the shampoo to form a thickened solution having a Brookfield viscosity of 26,750 cps (#4 @12 rpm @25° C.).

COMPARATIVE EXAMPLE 2

About 1.2 grams of pentaerythritol PEG-130 tetra isostearate were added to 60 grams of shampoo formulation A. The thickener dissolved in the shampoo after heating at 70° C. for one hour to form a thickened solution having a Brookfield viscosity of 27,750 cps (#4 @12 rpm @25° C.).

COMPARATIVE EXAMPLE 3

About 1.2 grams of pentaerythritol PEG-130 tetra isostearate were added to 60 grams of shampoo formulation A at a temperature of 25° C. The thickener did not dissolve in the shampoo after mixing at 25° C. for 24 hours.

What is claimed is:

1. A method of thickening an aqueous-based formulation which comprises adding to said aqueous formulation a thickening-effective amount of a composition comprising: (a) from about 10% to about 25% by weight of a cosolvent selected from the group consisting of a diol, the mono alkyl ether of a diol, a salt of a sulfated ethoxylated alcohol, a salt of a sulfated ethoxylated alkyl phenol, and a complex organic phosphate ester; (b) from about 5% to about 25% by weight of water; (c) from about 20% to about 60% by weight of a nonionic surfactant having an HLB of less than about 14; (d) from about 25% to about 60% by weight of an ester of an ethoxylated polyol having at least 3 alcohol groups and having degree of ethoxylation from about 80 to about 400.

2. The method of claim 1 wherein said nonionic surfactant is an alkyl polyglycoside of the formula I $$R_1O(Z)_a \qquad \text{I}$$

wherein $R_1$ is a monovalent organic radical having from about 6 to about 30 carbon atoms; Z is saccharide residue having 5 or 6 carbon atoms; a is a number having a value from 1 to about 6.

3. The method of claim 2 wherein said nonionic surfactant is an alkyl polyglycoside wherein the alkyl group contains 8 to 10 carbon atoms and having an average degree of polymerization of 1.7.

4. The method of claim 2 wherein said nonionic surfactant is an alkyl polyglycoside wherein the alkyl group contains 8 to 16 carbon atoms and having an average degree of polymerization of 1.6.

5. The method of claim 2 wherein said nonionic surfactant is an alkyl polyglycoside wherein the alkyl groups contains 12 to 16 carbon atoms and having an average degree of polymerization of 1.6.

6. The method of claim 1 wherein said cosolvent is 1,2-propanediol, PEG-200, PEG-400, or methoxy PEG-350.

7. The method of claim 6 wherein said cosolvent is 1,2-propanediol.

8. The method of claim 1 wherein said cosolvent is the sodium salt of a sulfated polyethoxynonylphenol, the ammonium salt of a sulfated polyethoxynonylphenol, sodium salt of a sulfated alkylphenoxypolyethyleneoxy ethanol.

9. The method of claim 1 wherein said cosolvent is a complex organic phosphate ester.

10. The method of claim 1 wherein said ester of an ethoxylated polyol is pentaerythritol PEG-120 tetra C12–C18 ester, pentaerythritol PEG-90 tetra isostearate, pentaerythritol PEG-130 tetra isostearate or pentaerythritol PEG-120 tetra isostearate.

11. The method of claim 1 wherein said nonionic surfactant is a combination of nonionic surfactants selected from the group consisting of: (a) a mixture of an alkyl polyglycoside and an ethoxylated alkyl phenol; (b) a mixture of an alkyl polyglycoside and an ethoxylated fatty alcohol.

12. The method of claim 1 wherein said nonionic surfactant is a combination of nonionic surfactants comprised of decyl alcohol EO-6 and an alkyl polyglycoside wherein the alkyl group contains 8 to 10 carbon atoms and having an average degree of polymerization of 1.7.

13. The method of claim 1 wherein said nonionic surfactant is a combination of nonionic surfactants comprised of decyl alcohol EO-6 and an alkyl polyglycoside the alkyl group contains 8 to 16 carbon atoms and having an average degree of polymerization of 1.6.

14. The method of claim 1 wherein said nonionic surfactant is a combination of nonionic surfactants comprised of nonyl phenol EO-9 and an alkyl polyglycoside wherein the alkyl groups contains 12 to 16 carbon atoms and having an average degree of polymerization of 1.6.

15. The method of claim 1 wherein said nonionic surfactant is a combination of nonionic surfactants selected from the group consisting of: (a) an alkyl polyglycoside and nonylphenol EO-9; (b) an alkyl polyglycoside and decyl alcohol EO-6.

16. The method of claim 1 wherein said ester of an ethoxylated polyol is present in an amount up to 50% by weight.

17. A method of thickening an aqueous-based formulation which comprises adding to said aqueous formulation a thickening-effective amount of a composition comprising: (a) from about 1.0% to about 25% by weight of 1,2-propanediol; (b) from about 5% to about 25% by weight of water; (c) from about 20% to about 60% by weight of a nonionic surfactant selected from the group consisting of nonylphenol EO-9, decyl alcohol EO-6, an alkyl polyglycoside of the formula I $$R_1O(Z)_a \qquad\qquad I$$

wherein $R_1$ is a monovalent organic radical having from about 6 to about 30 carbon atoms; Z is saccharide residue having 5 or 6 carbon atoms; a is a number having a value from 1 to about 6, and combinations thereof; (d) from about 25% to about 60% by weight of an ester of an ethoxylated polyol selected from the group consisting of pentaerythritol PEG-120 tetra C12–C18 ester, pentaerythritol PEG-90 tetra isostearate, pentaerythritol PEG-130 tetra isostearate, pentaerythritol PEG-120 tetra isostearate and combinations thereof.

* * * * *